(12) United States Patent
Li et al.

(10) Patent No.: US 6,673,618 B1
(45) Date of Patent: *Jan. 6, 2004

(54) METHOD FOR MEASUREMENT OF NUCLEATED RED BLOOD CELLS

(75) Inventors: Yi Li, Miami, FL (US); Jing Li, Miami, FL (US); Ted W. Britton, Sunrise, FL (US)

(73) Assignee: Coulter International Corp., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/226,800

(22) Filed: Aug. 23, 2002

Related U.S. Application Data

(63) Continuation-in-part of application No. 10/165,699, filed on Jun. 7, 2002, now abandoned, which is a continuation of application No. 09/917,533, filed on Jul. 27, 2001, now Pat. No. 6,410,330.

(51) Int. Cl.[7] .............................................. G01N 31/00
(52) U.S. Cl. ............................... 436/10; 436/8; 436/17; 436/63; 436/149; 436/150; 436/164; 422/73; 422/82.01; 422/82.02; 422/82.09; 435/2; 435/29; 435/34; 435/39
(58) Field of Search ................................ 436/8, 10, 17, 436/18, 63, 149, 150, 164; 422/73, 82.01, 82.02, 82.05, 82.09; 435/2, 4, 29, 34, 39

(56) References Cited

U.S. PATENT DOCUMENTS

| | | |
|---|---|---|
| 2,656,508 A | 10/1953 | Coulter |
| 3,810,011 A | 5/1974 | Coulter et al. |
| 5,242,832 A | 9/1993 | Sakata |
| 5,298,426 A | 3/1994 | Inami et al. |
| 5,559,037 A | 9/1996 | Kim et al. |
| 5,648,225 A | 7/1997 | Kim et al. |
| 5,763,280 A | 6/1998 | Li et al. |
| 5,874,310 A | 2/1999 | Li et al. |
| 5,879,900 A | 3/1999 | Kim et al. |
| 5,882,934 A | 3/1999 | Li et al. |
| 5,917,584 A | 6/1999 | Li et al. |
| 6,228,652 B1 * | 5/2001 | Rodriguez et al. ............ 436/63 |
| 6,410,330 B1 | 6/2002 | Li et al. |
| 6,472,215 B1 * | 10/2002 | Huo et al. .................... 436/10 |

FOREIGN PATENT DOCUMENTS

| | | |
|---|---|---|
| EP | 1004880 A2 | 5/2000 |
| WO | WO 95/24651 | 9/1995 |

* cited by examiner

*Primary Examiner*—Maureen M. Wallenhorst
(74) *Attorney, Agent, or Firm*—Mitchell E. Alter

(57) ABSTRACT

A method for differentiating and enumerating nucleated red blood cells in a blood sample is described. The method includes the steps of lysing red blood cells of a blood sample with a lytic reagent, measuring nucleated blood cells by DC impedance measurement in a non-focused flow aperture, differentiating nucleated red blood cells from other cell types, and reporting nucleated red blood cells in the blood sample. The method further includes subtracting nucleated red blood cells and other interference materials from the count of remaining blood cells, and reporting a corrected white blood cell count of the blood sample. Additionally, the method further includes measuring spectrophotometric absorbance of the sample mixture at a predetermined wavelength of a hemoglobin chromogen formed upon lysing the blood sample, and reporting hemoglobin concentration of the blood sample.

6 Claims, 8 Drawing Sheets

METHOD FOR MEASUREMENT OF NUCLEATED RED BLOOD CELLS

This application is a continuation-in-part of application Ser. No. 10/165,699, filed on Jun. 7, 2002 and now abandoned, which is a continuation of application Ser. No. 09/917,533, filed on Jul. 27, 2001 and now U.S. Pat. No. 6,410,330, issued on Jun. 25, 2002.

FIELD OF THE INVENTION

The present invention relates to a method for determination of nucleated red blood cells in a blood sample. More specifically the method differentiates nucleated red blood cells from other cell types using a direct current impedance measurement in a non-focused flow aperture, and enumerates nucleated red blood cells in a blood sample.

BACKGROUND OF THE INVENTION

Normal peripheral blood contains mature red blood cells which are free of nucleus. Nucleated red blood cells (NRBCs), or erythroblasts, are immature red blood cells. They normally occur in the bone marrow but not in peripheral blood. However, in certain diseases such as anemia and leukemia, NRBCs also occur in peripheral blood. Therefore, it is of clinical importance to measure NRBCs. Traditionally, differentiation and enumeration of NRBC are performed manually. The process involves the smearing of a blood sample on a microscope slide and staining the slide, followed by manual visual analysis of the individual slide. The NRBC concentration is reported as numbers of NRBC per 100 white blood cells. Usually, 200 white blood cells and the numbers of NRBC present in the same region on a blood smear are counted and the numbers are divided by 2 to express the NRBC concentration as the numbers of NRBC/100 WBC. This approach is extremely time-consuming as well as being subjective to the interpretation of the individual analyzing the slide.

In recent years, several fluorescence flow cytometry methods have been developed for differentiating NRBCs. These methods utilizes specific nuclear staining technique to distinguish NRBCs from other cell types because it is difficult to differentiate NRBCs based on their electronic or optical properties.

U.S. Pat. No. 5,298,426 (to Inami et al.) discloses a fluorescence method for differentiating NRBCs. The method utilizes a two-step staining using a first fluid and a second fluid. Inami et al. teaches that the first fluid contains an erythroblast-staining dye that diffuses into nucleated red blood cells to specifically stain their nuclei, and then separating a group of NRBCs from other cell groups on a two-dimensional plot whereby the results of NRBC differentiation are computed.

U.S. Pat. No. 5,559,037 (to Kim et al.) discloses a method for flow cytometric analysis of NRBCs and leukocytes. The method comprises lysis of red blood cells and NRBC cytoplasm from a whole blood sample to expose the NRBC nuclei to a vital nuclear stain and minimizing the permeation of the vital nuclear stain into the leukocytes and analyzing the sample by measuring fluorescence and two angles of light scatter. This method features a triple triggering method which blocks the signals from debris (fluorescent and non-fluorescent) and identifies the signals which fall below the ALL trigger but above the fluorescence trigger (FL3) as NRBCs. ALL is the axial loss of light or the light scatter signals detected at 0° from the incident light. Therefore, pre-gating signals in more than one dimension are required in this method for identification of NRBC population. In addition, the method requires heating of the reagent to 42° C. in order to obtain the NRBC and leukocyte differentiations.

U.S. Pat. No. 5,648,225 (to Kim et al) discloses a method of using a multipurpose lysing reagent for subclassification of nucleated blood cells. The method comprises the steps of lysing a blood sample with the multipurpose lysing reagent which contains a nuclear stain, incubating the sample mixture at an elevated temperature, and determining the nucleated blood cells including NRBCs with an automated electro-optical hematology instrumentation.

U.S. Pat. No. 5,879,900 (to Kim et al) discloses a method of differentiating NRBCs, damaged white blood cells (WBC), WBC and a WBC differential in a blood sample by flow cytometry. The method includes lysing a blood sample; staining NRBCs and any damaged white blood cells with a vital nuclear stain; analyzing the sample mixture by measuring at least one fluorescence, and at least one light scatter signals in a range from 0° to 1° and 3° to 10°; constructing a three-dimensional plot from the fluorescence and light scatter signals; and differentiating and enumerating WBC, NRBC, damaged WBC and a WBC subclass differential.

EP 1 004 880 A2 discloses reagents and a method for discrimination and counting of nucleated red blood cells. The method includes the steps of lysing red blood cells, staining white blood cells and NRBCs, assaying the sample by measuring at least one scattered light parameter, and at least one fluorescence parameter.

U.S. Pat. No. 5,874,310 (to Li et al) discloses a method for differentiation of nucleated red blood cells. The method includes lysing mature red blood cells and analyzing the sample in a flow cell by light scatter measurement to differentiate NRBCs from other cell types. The light scatter measurement is performed by using two low angle light scatter signals of less than 10°. The method further includes a concurrent differentiation of white blood cells using electronic and optical analysis, wherein the electronic analysis is a DC impedance measurement.

U.S. Pat. No. 5,917,584 (to Li et al) discloses a method for differentiation of nucleated red blood cells. The method includes lysing mature red blood cells in a blood sample; analyzing the sample in a flow cell by two angles of light scatter measurement to differentiate NRBCs from other cell types, wherein the second light scatter signal is a medium angle or a right-angle light scatter signal.

The above described methods enable differentiation and enumeration of NRBCs and leukocytes by fluorescence flow cytometry and light scatter measurements. However, fluorescence and light scatter measurements are complex and expensive detection methods.

Many current non-fluorescence automated hematology analyzers, such as Abbott Cell-Dyn® 3500, COULTER® Gen*S™, Bayer Advia*120®, and Sysmex™ NE-9000 are only able to provide NRBC flagging for the possible presence of NRBCs in an analyzed blood sample when the instruments sense an increased amount of signals near blood cell debris area of an obtained cell distribution histogram. However, such techniques frequently generate false positive flagging because many other blood abnormalities can cause increased signals at the same area, such as platelet clumps and sickle cells, as well as red cell debris from insufficiently lysed blood samples. In these methods NRBCs are not distinctly identified. Instead, only a common NRBC sample distribution pattern in a histogram or a dotplot is recognized by the instrument which can be confused with a similar pattern generated by above-mentioned other causes.

Furthermore, a well known problem with NRBC containing samples is erroneous white blood cell count (WBC) reported by hematology analyzers on these samples. Since the nuclear volumes of NRBC are close to those of white blood cells, and they are commonly counted as white blood cells on hematology analyzers which measure the sizes of blood cells, resulting an elevation of WBC. Therefore, correction of NRBC contribution to the WBC reported from hematology analyzer is required for samples containing NRBC. Current practice in the clinical laboratory is to subtract the numbers of NRBC obtained by manual count from the WBC count reported by the hematology analyzers. This is time consuming and error prone.

On the other hand, measurement of hemoglobin (Hgb) concentration of blood samples is an integral part of blood analysis, which is important for disease diagnosis and for monitoring responses to medical treatment. It is desirable to be able to accomplish multiple diagnostic analyses such as enumerating nucleated blood cells and measuring hemoglobin concentration of a blood sample using the same reagent and concurrent measurements.

Among the many well known methods for hemoglobin determination, the cyanmethemoglobin method has been recommended as a standard by the International Committee for Standardization in Hematology. However, the presence of cyanide in the reagent waste has caused enormous environmental concern. In last ten years, a tremendous effort has been given to develop automated hemoglobin analysis methods without utilizing cyanide.

U.S. Pat. No. 5,242,832 (to Sakata) discloses a method using a cyanide-free lysing reagent for counting white blood cells and measuring the hemoglobin concentration in blood samples. PCT/US95/02897 (to Kim) discloses a cyanide-free method and reagent for determining hemoglobin in a whole blood sample. No capability of counting leukocytes, nor differentiating nucleated red blood cells is taught by Kim. U.S. Pat. Nos. 5,763,280 and 5,882,934 (to Li et al) disclose cyanide-free reagents for measuring hemoglobin in a blood sample, counting leukocytes, and differentiating leukocyte subpopulations. However, none of the above described hemoglobin measurement methods enables differentiation of nucleated red blood cells from other cell types.

Based on foregoing, there exists a need for a simple and less costly analysis method for differentiating and enumerating nucleated red blood cells. Furthermore, it is desirable to have a multifunctional test method for enumeration of nucleated blood cells, differentiation of nucleated red blood cells from other cell types, and measurement of hemoglobin concentration in one concurrent test.

SUMMARY OF THE INVENTION

In one embodiment, the present invention relates to a method of differentiating nucleated red blood cells from other cell types in a blood sample. The method comprises steps of mixing a blood sample with a lytic reagent to lyse red blood cells, and to form a blood sample mixture; measuring the blood sample mixture by a DC impedance measurement in a non-focused flow aperture, and obtaining a blood cell distribution of the blood sample mixture; differentiating nucleated red blood cells from other cell types; and reporting nucleated red blood cells in the blood sample. The non-focused flow aperture has an aperture aspect ratio of 0.7 and greater. Reporting nucleated red blood cells includes reporting the presence of nucleated red blood cells in the blood sample, and reporting numbers of nucleated red blood cells per one hundred of white blood cells in the blood sample, or numbers of nucleated red blood cells in an unit volume of the blood sample.

In a further embodiment, the present invention relates to a method of correcting white blood cell count. The method comprises the steps of mixing a blood sample with a lytic reagent to lyse red blood cells, and to form a blood sample mixture; measuring the blood sample mixture by a DC impedance measurement to obtain a blood cell distribution and a count of remaining blood cells; differentiating nucleated red blood cells and other interference materials from white blood cells; subtracting nucleated red blood cells and other interference materials from the count of remaining blood cells; and reporting a corrected white blood cell count in the blood sample. The method further comprises reporting nucleated red blood cells in the blood sample.

In another embodiment, the present invention relates to a method of concurrently differentiating nucleated red blood cells, enumerating white blood cells, and measuring hemoglobin concentration of a blood sample. The method comprises steps of mixing a blood sample with a lytic reagent to lyse red blood cells, and to form a blood sample mixture; measuring the blood sample mixture by a DC impedance measurement to obtain a blood cell distribution and a count of remaining blood cells; differentiating nucleated red blood cells and other interference materials from white blood cells; subtracting nucleated red blood cells and other interference materials from the count of remaining blood cells; measuring spectrophotometric absorbance of the blood sample mixture at a predetermined wavelength of a hemoglobin chromogen formed upon lysing the blood sample; reporting the nucleated red blood cells in the blood sample; reporting numbers of white blood cells in the blood sample; and reporting a hemoglobin concentration of the blood sample.

DETAILED DESCRIPTION OF THE INVENTION

Figure 1A:
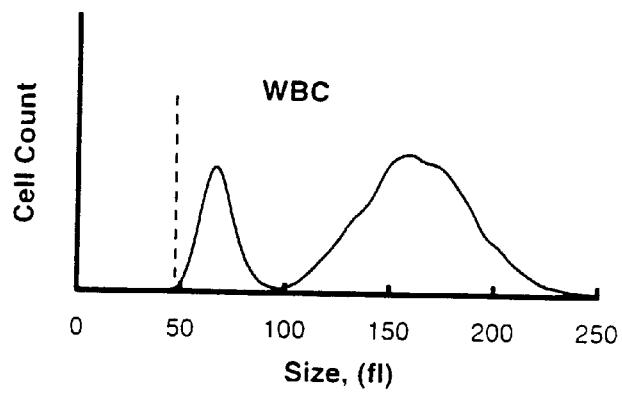
FIGS. 1A, 1B and 1C are the DC histograms of a normal blood sample and two clinical abnormal blood samples containing nucleated red blood cells, respectively. The samples were processed according to the procedure described in Example 1 and analyzed on an experimental hematology analyzer using non-focused flow apertures having a length of $120\mu$ and a width of $100\mu$.

The first embodiment of the present invention is directed to a method for differential analysis of nucleated red blood cells. More specifically the method enables differentiation of nucleated red blood cells from other cell types in a blood sample by a direct current impedance measurement with a non-focused flow aperture.

A method of differentiating nucleated red blood cells from other cell types in a blood sample comprising steps of: mixing a blood sample with a lytic reagent to lyse red blood cells, and to form a blood sample mixture; measuring said blood sample mixture by a DC impedance measurement in a non-focused flow aperture, and obtaining a blood cell distribution of said blood sample mixture; and differentiating nucleated red blood cells (NRBCs) from other cell types.

To lyse a blood sample, the blood sample can be diluted first by a blood diluent, then mixed with a sufficient amount of a lytic reagent to lyse red blood cells. For the purpose of the present invention, the blood diluent contains a sufficient amount of salt or salts for impedance measurement of the sample mixture. Suitable examples of salts are alkaline metal salts.

A blood diluent is commonly used on a hematology analyzer to dilute a blood sample for measuring red blood cells, where the blood diluent is adjusted to isotonic by salts for maintaining the blood cell volumes. It is convenient to use commercially available isotonic blood diluents for the purpose of the present invention, although isotonicity is not required for differential analysis of NRBCs.

A lytic reagent suitable to use with a blood diluent for the present invention comprises an aqueous solution of:

(a) a quaternary ammonium salt or salts, represented by following molecular structure:

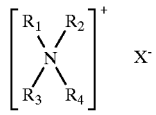

wherein $R_1$ is an alkyl, alkenyl or alkynyl group having 12 to 16 carbon atoms; $R_2$, $R_3$ and $R_4$ are alkyl groups having 1 to 4 carbon atoms and $X^-$ is chloride or bromide anion;

(b) an ethoxylated alkyl phenol, wherein the alkyl group has 6 to 12 carbon atoms, and the number of ethylene oxide is in a range from about 10 to about 50; and (c) an ethoxylated alcohol represented by following molecular structure:

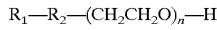

wherein $R_1$ is an alkyl, alkenyl or alkynyl group having 10 to 22 carbon atoms, $R_2$ is —O—, and n is between 20 and 35.

Suitable examples of quaternary ammonium salts are tetradecylammonium bromide, hexadecyltrimethylammonium bromide and dodecyltrimethylammonium chloride. Suitable examples of ethoxylated alcohol are Plurofac A38 prill surfactant, from BASF Corp., New Jersey, and Hetoxol STA-30, from Heterene, Inc., New Jersey. Suitable examples of ethoxylated phenol is Igepal SS-837, from Rhône-Poulenc, New Jersey, and Chemax NP-30, from Chemax Inc., South Carolina.

Alternatively, a lytic reagent further containing a sufficient amount of a salt or salts for impedance measurement can be used for lysing a blood sample without a separate blood diluent. Suitable examples of salts are alkaline metal salts, such as sulfates, chlorides, phosphates, and citrates.

The differential analysis of NRBCs is performed in a non-focused flow aperture using DC impedance measurement. When a particle, such as a blood cell, passes through the aperture, an electrical signal can be measured due to conductivity or impedance change. The pulse shape, height and width, is directly related to the size of a particle, and can be converted to the size of the particles measured. When two or more particles of different sizes are measured, the histogram obtained from the measurement can represent size distribution of the particles.

The detection methods used for blood cell counting and sizing by a blood analyzer equipped with a DC impedance measurement device are generally described in U.S. Pat. No. 2,656,508 (to Coulter), and U.S. Pat. No. 3,810,011 (to Coulter, et al), which are hereby incorporated by reference in its entirety.

It is found that the aperture aspect ratio, defined as a ratio of the aperture length versus the aperture width, affects the separation of different sizes of blood cells, in particular the NRBC population from other nucleated blood cells. With the method of the present invention, separation of the NRBC population from the other cell types can be achieved by using an aperture aspect ratio of 0.7 and greater.

It has been understood that aperture aspect ratio affects the flow profile of a flow passing through the aperture, which in turn, affects trajectory of particles in the flow. In general, with a fixed aperture width, the rate of a flow at the center of the flow increases with increasing the length of the aperture. Therefore, with an increase of the aperture aspect ratio, a flow rate gradient, from the sides of the flow which interface with the wall of aperture toward center of the flow, increases. In the presence of such a flow rate gradient, particles suspended in a flow passing through the aperture tend to move to the center of the flow. Therefore, under such a condition, particles have a similar behavior to the particles passing through a focused flow aperture. A focused flow aperture can be used in the present invention for measuring nucleated blood cells, particularly for differentiating blood cells having similar sizes. However, the cost of a focused flow aperture is much higher than a non-focused flow aperture.

On the other hand, it is known that at a cross section of an aperture, an imposed electrical field has a different strength along the cross section. Consequently, the particles passing through a non-focused flow aperture can generate various pulse shapes because each particle may experience a different electrical field depending on its position along the cross section of the aperture. These pulse distortions cause distortion of the particle size distribution in the measured histogram. Historically, pulse editing has been broadly used in the art to edit out seriously distorted pulses, and improve particle size differentiation to a certain degree. It is understood that with increase of the aperture aspect ratio, electrical field gradient along the cross section, from the center to the side wall of the aperture, decreases. Consequently, electrical pulses generated from the particles not passing the center of the aperture have less distortions because of the presence of a more homogeneous electrical field along the cross section.

Therefore, with an increase of aperture aspect ratio the two effects, control of particle trajectory in the non-focused flow aperture and reduction of electrical field gradient along the cross section of the aperture, improve ability of differentiation of different sizes of particles.

It has been found using a non-focused flow aperture with an aperture aspect ratio of 0.7 and greater, the NRBC population can be differentiated from closely sized other nucleated blood cells, particularly lymphocytes. Preferably, an aperture aspect ratio of 1.0 and greater is used. More preferably, an aperture aspect ratio about 1.2 is used.

To further increase the aperture aspect ratio, the separation of NRBC from other cell types can be further improved. However, when the aperture aspect ratio is 1.5 or above, the throughput of the sample mixture passing through the aperture for measurement reduces significantly, and it can render the measurement incompatible to the throughput requirement of a hematology instrument. Therefore, it should be understood that an aperture aspect ratio about 1.2 is selected based on a balance between the population separation and throughput of the measurement for a practical reason. Theoretically, an aperture aspect ratio above 1.2 can be used for separating the NRBCs from other cell types.

Figure 1B:
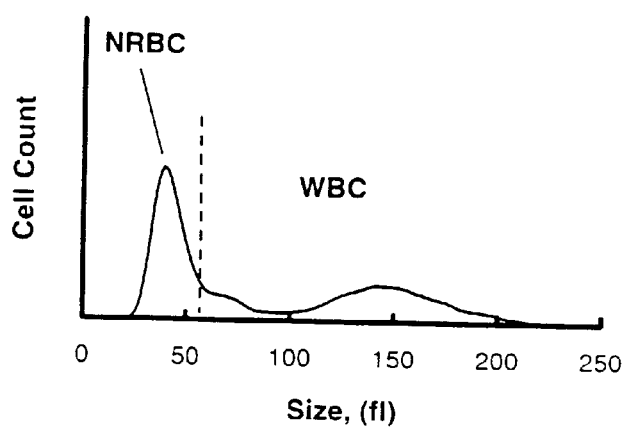
Figure 1C:
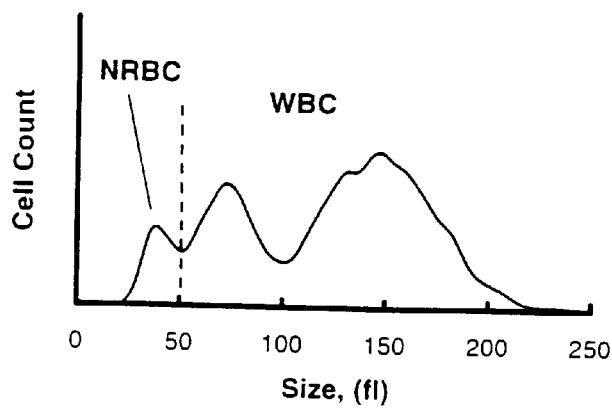

FIGS. 1A, 1B and 1C show DC histograms of blood samples processed according to the method of the present invention, following the procedure described in Example 1, and analyzed on an experimental hematology analyzer using non-focused flow apertures having a length of $120\mu$ and a width of $100\mu$. The aperture aspect ratio is 1.2. FIG. 1A is a histogram of a normal blood sample. As shown, a normal blood sample, after lysing the red blood cells with a lytic reagent, exhibits a bi-module distribution of the nucleated blood cells. In this case, all nucleated blood cells are from the white blood cells. The major cell population in the left peak is lymphocytes. On the left side of this peak, the area of the histogram is clean.

FIGS. 1B and 1C are histograms of two clinical abnormal blood samples containing nucleated red blood cells. The blood samples shown in FIGS. 1B and 1C contain 230 NRBC/100 WBC and 9 NRBC/100 WBC, respectively, determined by the manual reference method. The NRBC population shows as an additional peak on the left side of white blood cells.

Figure 2A:
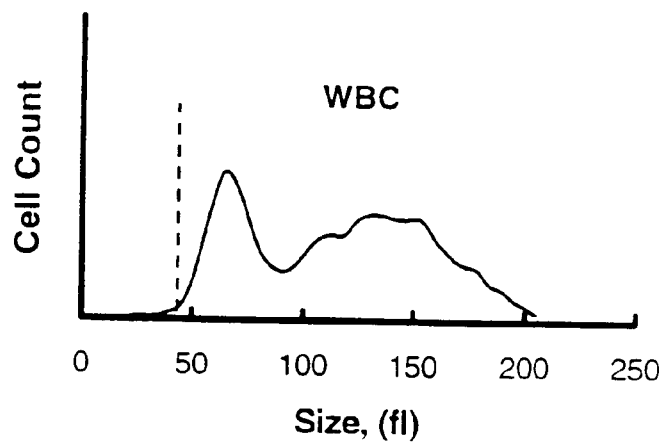
FIGS. 2A and 2B show histograms of a normal blood sample and a clinical sample containing nucleated red blood cells. The samples were processed according to the procedure described in Example 2 and analyzed on an experimental hematology analyzer using a non-focused flow aperture having a length of $70\mu$ and a width of $100\mu$.
Figure 2B:
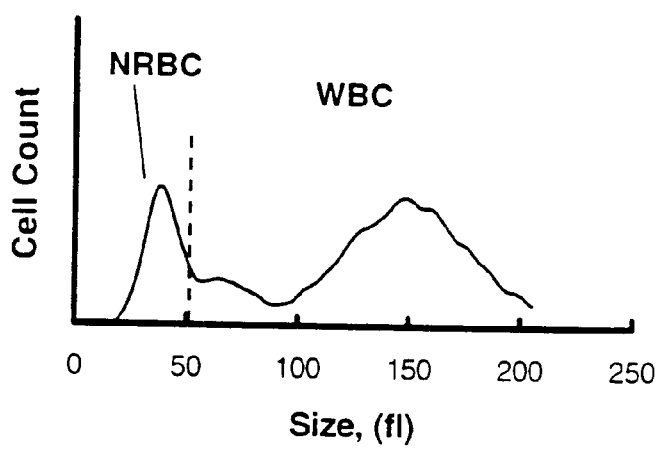

FIGS. 2A and 2B show histograms of a normal blood sample and a clinical sample containing nucleated red blood cells processed according the procedure described in Example 2, and analyzed using a non-focused flow aperture having a length of $70\mu$ and a width of $100\mu$. The aperture aspect ratio is 0.7. This experimental hematology analyzer has a different signal amplification scale from the analyzer used in Example 1. As shown, the NRBC population appears on the left of white blood cells.

Figure 3A:
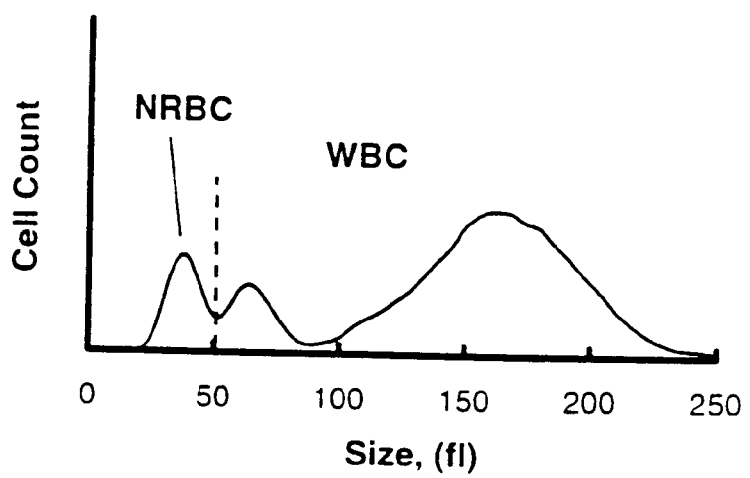
FIGS. 3A and 3B show histograms of a clinical sample containing nucleated red blood cells processed according to the procedure described in Example 1 and analyzed on two experimental hematology analyzers using non-focused flow apertures having a length of $120\mu$ and a width of $100\mu$, and a length of $85\mu$ and a width of $70\mu$, respectively.
Figure 3B:
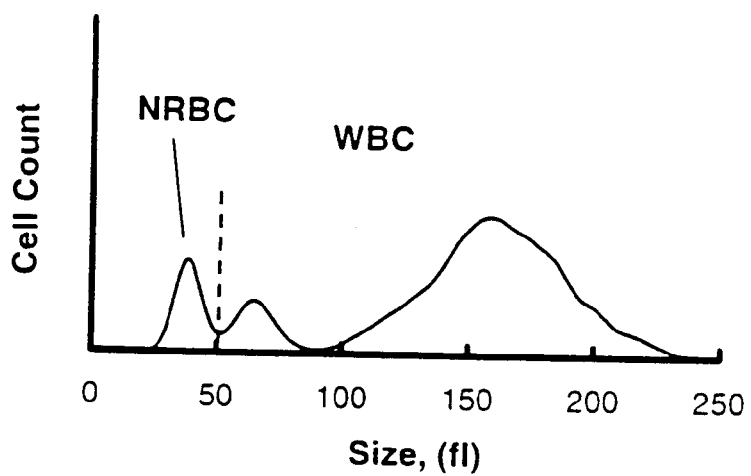

FIGS. 3A and 3B show histograms of a clinical sample containing nucleated red blood cells processed following the procedure described in Example 1, and analyzed on two experimental hematology analyzers, as described in Example 3. The histogram shown in FIG. 3A was obtained using non-focused flow apertures having a length of $120\mu$ and a width of $100\mu$. The histogram shown in FIG. 3B was obtained using non-focused flow apertures having a length of $85\mu$ and a width of $70\mu$. Although the two types of apertures are substantially different in length and width, they both have the same aperture aspect ratio of 1.2. Apparently, the two histograms show a similar population distribution. In both cases, differentiation of NRBC population from other nucleated blood cells is achieved.

Using the method of the present invention, since NRBC population is differentiated from other cell types, particularly from the white blood cells, the presence of NRBC population in a sample analyzed can be identified and reported. To report the presence of clinically abnormal populations in a blood sample is often called flagging on hematology analyzers, which is an important feature for assisting clinical diagnosis.

Furthermore, using the method of the present invention the NRBC population can be enumerated. When the threshold of a DC detector is set below the size of NRBCs as shown in the figures, the NRBC population can be enumerated together with white blood cells. After differentiating the NRBC population from other cell types based on the population distribution of an obtained DC histogram, NRBC concentration of an analyzed sample can be calculated. The NRBC concentration can be reported as the numbers of NRBC per hundred of white blood cells (NRBC/100 WBC), which is the same unit of the manual reference. Alternatively, the numbers of NRBC can also be reported as an absolute number per unit volume of a blood sample by multiplying the ratio with WBC count of the blood sample.

In a further embodiment of the present invention, the method can further comprise correction of white blood cell counts. Historically, when white blood cells are counted using a direct current impedance method, the NRBCs are counted, or partially counted with white blood cells because they are not differentiated from other nucleated blood cells. The interference caused by NRBCs can result in elevated and erroneous white blood cell counts. With the method of the present invention, upon differentiating the NRBCs, the contribution of this population to the white blood cell count can be subtracted from the total count of nucleated blood cells.

Additionally, it is known that some blood samples are more difficult to lyse than normal blood samples. In some cases, if blood cell membranes do not dissolve sufficiently during sample preparation to the sizes below the DC detection threshold, cell debris can also interfere the white blood cell count. Usually, cell debris has relatively small volumes, and it appears on the left of NRBCs on the histogram.

However, with the method of the present invention the interference materials can be better separated from the white blood cells because of improved separations among different cell types, and can be subsequently removed from the total count of the remaining blood cells in the sample mixture. Therefore, a corrected white blood cell count can be reported by the method.

The term of interference materials has a broad meaning herein, which includes any particulate materials that are not white blood cells, but measured in the sample mixture by the DC impedance measurement during the measurement of white blood cells.

In an additional embodiment, the present invention also relates to a method of concurrently differentiating nucleated red blood cells, and measuring hemoglobin concentration of a blood sample. The method comprises the steps of (a) mixing a blood sample with a lytic reagent to lyse red blood cells, and to form a blood sample mixture, (b) measuring the blood sample mixture by a DC impedance measurement in a non-focused flow aperture, and obtaining a blood cell distribution of the blood sample mixture, (c) differentiating nucleated red blood cells from other cell types, (d) measuring spectrophotometric absorbance of the blood sample mixture at a predetermined wavelength of a hemoglobin chromogen formed upon lysing the blood sample, (e) reporting the presence of nucleated red blood cells, and (f) reporting hemoglobin concentration of the blood sample. As described previously, the method can further enumerate NRBCs and report numbers of NRBCs per hundred white blood cells.

Furthermore, the method can further include steps of obtaining a count of remaining blood cells by the DC impedance method, subtracting nucleated red blood cells from the count of remaining blood cells, and reporting numbers of white blood cells in the blood sample.

The method of measuring nucleated blood cells by a DC impedance measurement in a non-focused flow aperture, and differentiating nucleated red blood cells from other cell types has been described above. To concurrently measure hemoglobin concentration of the blood sample, the lysing reagent comprises a hemoglobin ligand which forms a stable hemoglobin chromogen upon lysing the red blood cells. Suitable ligands include tetrazole and derivatives, imidazole and its derivatives, alkaline salts of benzoic acid and derivatives, and quinaldic acid. A description of these ligands can be found in U.S. Pat. No. 5,763,280 (to Li et al), and which is hereby incorporated by reference in its entirety. Suitable examples of imidazole derivatives are methylimidazole, and ethylimidazole. Alternatively, the hemoglobin ligands can be added in a blood diluent if the diluent is used to dilute the blood sample as described previously. Moreover, a lytic reagent containing a salt or salts, which enables impedance measurement without using a separate blood diluent, can also include the hemoglobin ligands for the hemoglobin measurement. Example 4 illustrates such an example of the method that enables differentiation of NRBCs and measuring hemoglobin concentration of a blood sample using a single lytic reagent without a separate blood diluent.

The total hemoglobin concentration of the blood sample can be determined by measuring spectrophotometric absorption of the blood sample mixture at a predetermined wavelength. The wavelengths are different for different hemoglobin chromogens. With the ligands described above, the absorptions can be measured between about 510 nm and about 560 nm.

The utility of the method of the present invention in analyzing clinical samples is demonstrated in Example 5. Totally 95 normal and 74 clinical whole blood samples containing NRBCs were analyzed on an experimental hematology analyzer with the instrument configuration detailed in Example 1, using the lytic reagent composition of Example 5 and Isoton® III as diluent. The same samples were also analyzed by COULTER® GEN*S hematology analyzer, and COULTER COUNTER® ZBI as references. The numbers of NRBC per 100 WBC were obtained from a 500 cell manual count following NCCLS standard method, and used as the reference.

The DC histograms obtained on the experimental hematology analyzer were analyzed by an experimental algorithm to differentiate the NRBCs from the white blood cells, and to report the numbers of NRBC per 100 WBC. Then the NRBCs were subtracted from the total nucleated cells counted to obtain a correct WBC count.

Figure 5A:
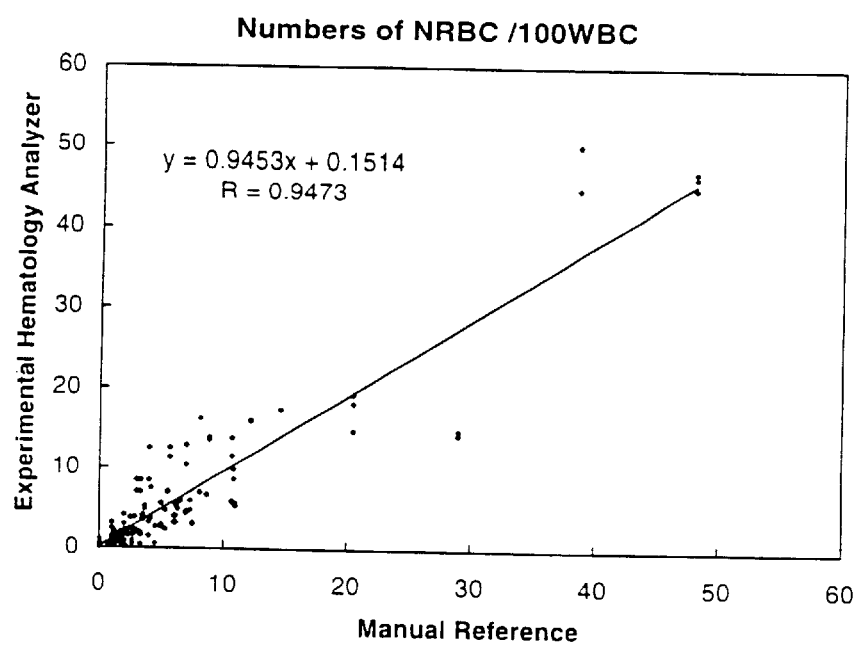
FIG. 5A shows the correlation of NRBC concentration obtained by the method of the present invention described in Example 5 to the manual reference results.

FIG. 5A shows the results of NRBC enumeration, which demonstrates a good linear correlation between the results obtained using the method of the present invention and the manual reference.

Figure 5B:
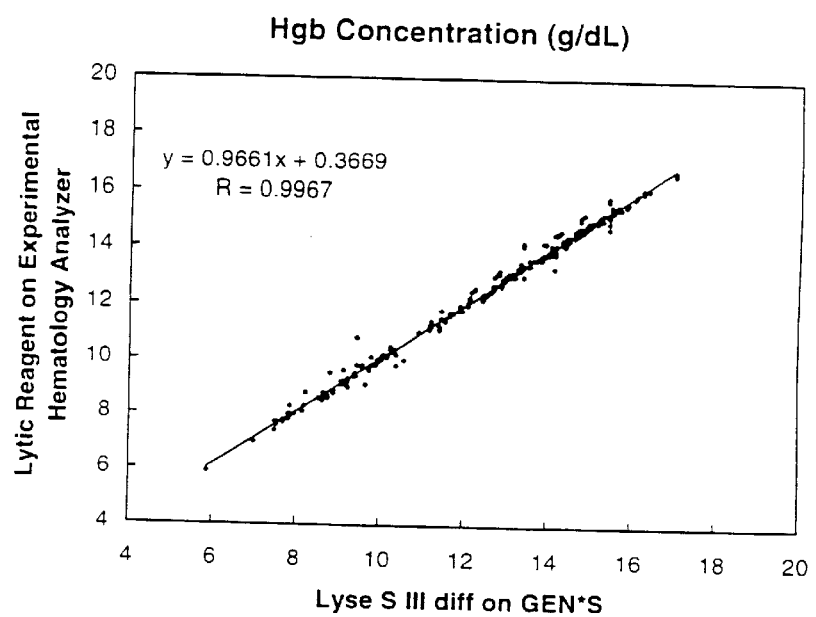
FIG. 5B shows the correlation of the hemoglobin concentration obtained using the method of the present invention described in Example 5 to that obtained on COULTER Gen*S.

FIG. 5B shows the correlation between hemoglobin concentration obtained by the method described in the example and that obtained on COULTER® GEN*S. The results demonstrate an excellent linear correlation for hemoglobin measurement.

Example 6 further demonstrates the present invention for differentiating nucleated red blood cells from white blood cells and further differentiating subpopulations of white blood cells such as lymphoid and myelold subpopulations.

Figure 5C:
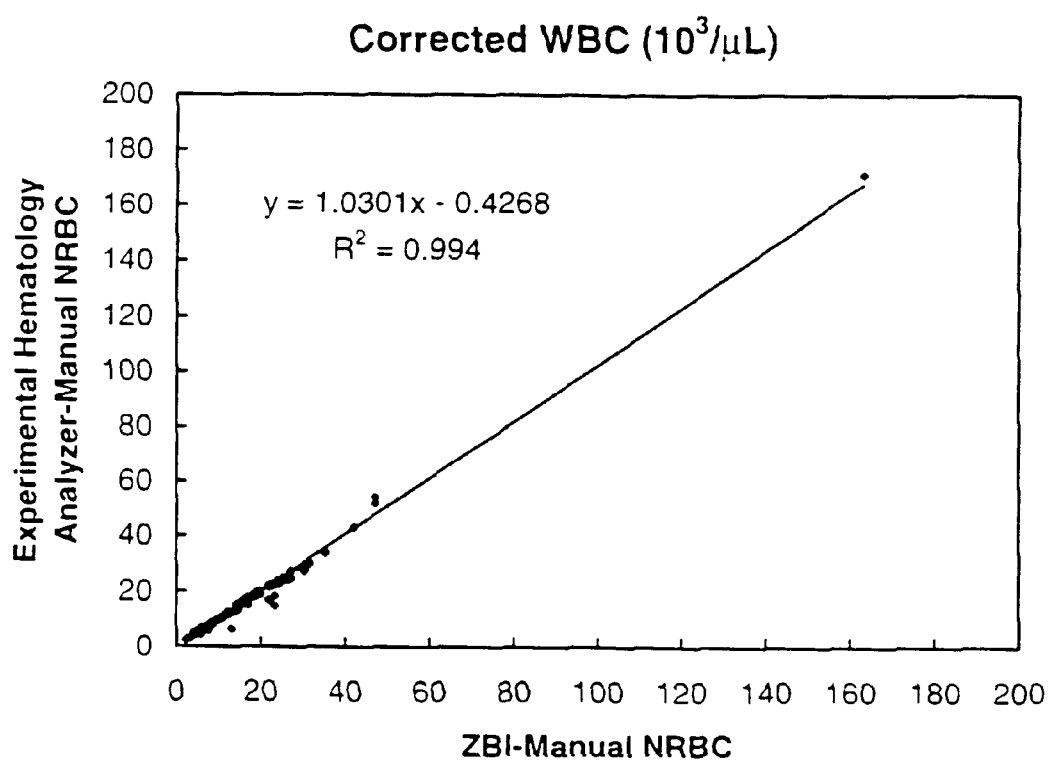
FIG. 5C shows the correlation of corrected WBC obtained using the method of the present invention described in Example 5 to the corrected WBC obtained by correcting the count obtained on COULTER COUNTER® ZBI with manual NRBC count.

FIG. 5C shows the correlation of the corrected WBC count between the reference and the results obtained by the method of the present invention. The reference results were obtained by subtracting the manual NRBC results from the WBC count obtained on the COULTER COUNTER® ZBI. As shown, the results obtained by the method of the present invention correlate excellently to the reference.

In a further aspect, the present invention is directed to an apparatus for differentiating nucleated blood cells in a blood sample. The apparatus comprises (a) means for mixing a blood sample with a lytic reagent system to lyse red blood cells and to form a blood cell sample mixture; (b) means for measuring the blood sample mixture by a DC impedance measurement in a non-focused aperture, and obtaining a blood cell distribution of the blood sample mixture; and (c) means for differentiating nucleated red blood cells from other cell types from obtained blood cell distribution. The non-focused aperture has preferably an aperture aspect ratio of 1.0 and greater.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

A reagent of the following composition was used for lysing a blood sample and for analyzing the nucleated blood cells.

| | |
|---|---|
| tetradecyltrimethylammonium bromide | 25.0 g |
| Igepal SS-837 (from RhÔne-Poulenc) | 15.0 g |
| Plurofac A38 prill surfactant (from BASF Corp.) | 4.0 g |
| distilled water adjusted to 1 liter | |
| pH | 5.0 |

28 $\mu$l of a whole blood sample was aspirated by an experimental hematology analyzer, diluted with 6 ml of Isoton® III (Beckman Coulter, Inc., Miami, Fla.), then mixed with 1 ml of above lytic reagent composition to lyse red blood cells. The sample mixture was drawn through a set of three non-focused flow apertures (arranged in parallel) by a constant vacuum. The apertures had a length of 120$\mu$ and a width of 100$\mu$. The nucleated blood cells were counted by a DC impedance measurement, and a histogram of the blood cells, after pulse editing, was also produced (averaged from the measurements of three apertures).

FIG. 1A shows a histogram of a fresh normal blood obtained following the above procedure, which shows a bi-module distribution of the white blood cells. FIG. 1B and 1C show two clinical samples measured following the above procedure. The clinical samples contain 230 NRBC/100 WBC, and 9 NRBC/100 WBC, respectively. As seen, a distinct population of NRBC appears on the left side of the white blood cells. The NRBC population was differentiated from the white blood cells, and the ratio between the NRBCs and white blood cells (×100) was reported as the numbers of NRBC/100 WBC. Alternatively, the NRBC can also be reported as absolute count in the blood sample by incorporating the total count of white blood cells.

EXAMPLE 2

FIGS. 2A and 2B show two histograms of a normal blood sample and a clinical sample containing NRBCs, respectively, processed according the procedure described in Example 1, and measured on an experimental hematology analyzer which had a single non-focused flow aperture. The aperture had a length of 70μ and a width of 100μ. The aperture aspect ratio is 0.7. This experimental hematology analyzer has a different signal amplification scale from the analyzer used in Example 1. As shown, the NRBC population appears on the left of white blood cells.

EXAMPLE 3

FIGS. 3A and 3B show two histograms of a clinical sample containing NRBCs processed following the procedure described in Example 1, and measured on two experimental hematology analyzers which used same reagents, and instrument configurations except that one had non-focused flow apertures having a length of 120μ and a width of 100μ, and the other had non-focused flow apertures having a length of 85μ and a width of 70μ. The histogram shown in FIG. 3A was obtained using the non-focused flow aperture having a length of 120μ and a width of 100μ. The histogram shown in FIG. 3B was obtained using the non-focused flow apertures having a length of 85μ and a width of 70μ. Although the two types of apertures are substantially different in length and width, they have the same aspect ratio of 1.2. Apparently, the two histograms showed a similar population distribution. In both cases, differentiation of NRBC population from other nucleated cells was achieved.

EXAMPLE 4

A reagent of the following composition was prepared.

| | |
|---|---|
| tetradecyltrimethylammonium bromide | 3.48 g |
| Igepal SS-837 (from RhÔne-Poulenc) | 2.09 g |
| Plurofac A38 prill surfactant (from BASF Corp.) | 0.56 g |
| tetrazole | 0.28 g |
| $Na_2SO_4$ | 7.94 g |
| NaCl | 3.46 g |
| $Na_2EDTA$ | 0.09 g |
| ADA | 1.21 g |
| antimicrobials | 0.98 g |
| BHT (predissolved in ethanol) | 0.01 g |
| distilled water adjusted to 1 liter | |
| pH | 5.8 |
| Osmolality | 312 mOsm |

Figure 4A:
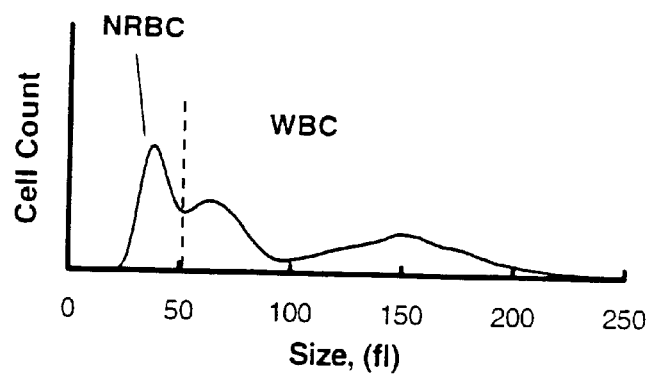
FIG. 4A shows a histogram of a whole blood sample obtained according to the procedure described in Example 4 using the lytic reagent composition of Example 4.

A clinical whole blood sample containing 31 NRBC/100 WBC (determined by manual reference method) was analyzed on the experimental hematology analyzer described in Example 1 with the same instrument configuration, but using the above lytic reagent composition as both the lysing reagent and the diluent. FIG. 4A shows the obtained histogram, which illustrates differentiation of NRBCs from white blood cells.

Figure 4B:
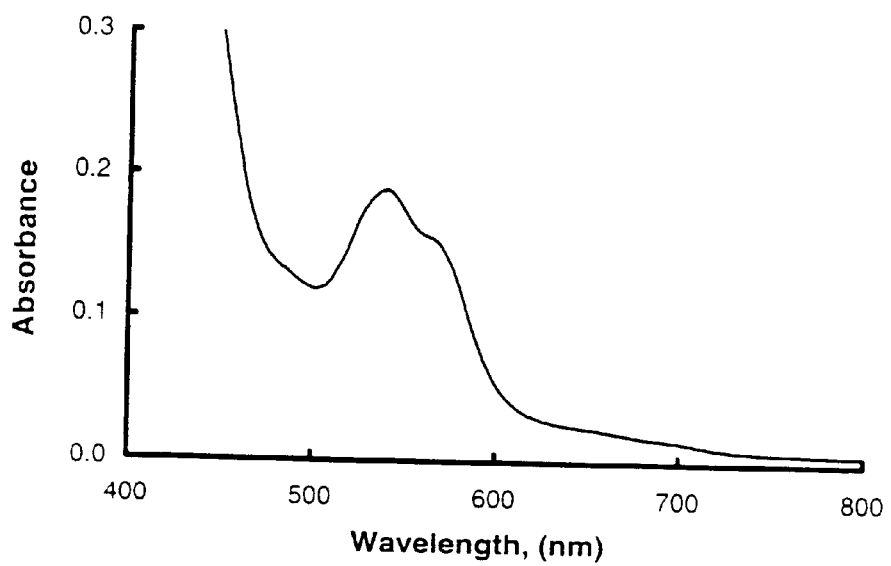
FIG. 4B shows a spectrum of the same sample processed with the lytic reagent composition of Example 4 according to the procedure described in Example 4.

Additionally, 11.6 μl of the same sample was diluted and mixed by 2903 μl of the above lytic reagent composition. The photometric absorption spectrum of the sample was measured immediately on a Beckman DU 7500 spectrophotometer. FIG. 4B is the obtained spectrum. As shown, the hemoglobin concentration of the sample can be measured between about 510 nm to about 560 nm.

EXAMPLE 5

A reagent of the following composition was prepared.

| | |
|---|---|
| tetradecyltrimethylammonium bromide | 25.0 g |
| Igepal SS-837 (from RhÔne-Poulenc) | 15.0 g |
| Plurofac A38 prill surfactant (from BASF Corp.) | 4.0 g |
| tetrazole | 2.0 g |
| BHT (predissolved in ethanol) | 0.04 g |
| distilled water adjusted to 1 liter | |
| pH | 2.9 |

95 normal and 74 clinical whole blood samples containing NRBCs were analyzed on the experimental hematology analyzer described in Example 1 except that the aperture had a length of 85μ and a width of 70μ. The analyzer uses the above lytic reagent and Isoton® III as diluent. The absorption of a sample mixture was also measured at 525 nm on the analyzer immediately after counting of the nucleated blood cells. Hemoglobin concentration of the sample was reported by the analyzer. Then the same samples were also analyzed by COULTER® GEN*S hematology analyzer, and COULTER COUNTER® ZBI. The COULTER® GEN*S was operated under its standard configuration according to manufacturer's manual, using Lyse S® III diff (Beckman Coulter, Inc. Miami, Fla.) as lysing reagent and Isoton® III as diluent. The white blood cells of the blood samples were counted on COULTER COUNTER® ZBI following NCCLS reference procedure for WBC count. The threshold on COULTER COUNTER® ZBI was set at 7.5 to ensure nucleated red blood cells being counted. A 500 cell manual count was obtained by three medical technologists for all clinical samples as a reference for nucleated red blood cells, and reported as numbers of nucleated red blood cells observed per 100 WBC counted (no. NRBC/100 WBC).

The DC histogram obtained was analyzed by an experimental algorithm to differentiate the NRBCs from the white blood cells, and to report the numbers of NRBC per 100 WBC. Then the NRBCs were subtracted from the total nucleated blood cells counted to obtain a correct WBC count.

FIG. 5A shows the results of NRBC enumeration obtained following the above process versus manual reference. The correlation coefficients, slopes and intercepts of the regression lines showed a good linear correlation for NRBC.

FIG. 5B shows the correlation between hemoglobin concentration obtained on the experimental hematology analyzer and that obtained on COULTER® GEN*S. The result demonstrates an excellent linear correlation for hemoglobin concentration.

FIG. 5C shows the correlation between the corrected WBC count obtained on the experimental hematology analyzer using procedure described above, and obtained by subtracting the manual NRBC results from the WBC count obtained on COULTER COUNTER® ZBI. The results illustrate an excellent correlation between the method of the present invention and the reference method.

EXAMPLE 6

A reagent of the following composition was used for lysing a blood sample and for analyzing the nucleated blood cells.

| | |
|---|---|
| tetradecyltrimethylammonium bromide | 35.0 g |
| Igepal SS-837 (from RhÔne-Poulenc) | 12.8 g |
| Sodium chloride | 9.0 g |
| Potassium cyanide | 0.25 g |
| distilled water adjusted to 1 liter | |
| pH | 9.3 |

28 μl of a whole blood sample was aspirated by an experimental hematology analyzer, diluted with 6 ml of Isoton® 3E (Beckman Coulter, Inc., Miami, Fla.), then mixed with 1 ml of above lytic reagent composition to lyse red blood cells. The sample mixture was drawn through a set of three non-focused flow apertures (arranged in parallel) by a constant vacuum. The apertures had a length of 100μ and a width of 83μ. The nucleated blood cells were counted by a DC impedance measurement, and a histogram of the blood cells, after pulse editing, was also produced (averaged from the measurements of three apertures).

Figure 6:
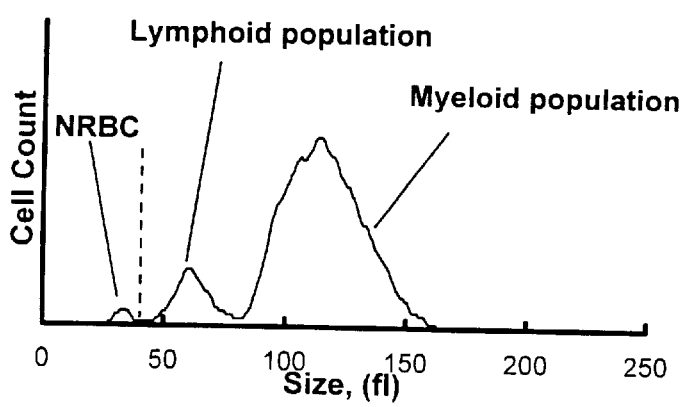
FIG. 6 shows a histogram of the present invention for differentiating nucleated red blood cells from white blood cells and further differentiating subpopulations of white blood cells such as lymphoid and myeloid subpopulations.

FIG. 6 shows a histogram of a clinical blood sample containing 4 NRBC/100 WBC obtained following the above procedure. As shown, three nucleated blood cell types are differentiated one from another. More specifically, the NRBC peak appears on the left side of the white blood cells. The white blood cells further differentiate into two subpopulations, lymphoid (lymphocytes) population and myeloid (neutrophils, monocytes, eosinophils, and basophils) population. This example illustrates utility of the method of the present invention for differentiating nucleated red blood cells from the white blood cells, and for differentiating subpopulations of white blood cells.

What is claimed is:

1. A method of analyzing a nucleated blood cells in a blood sample comprising the steps of:
    (a) mixing a blood sample with a lytic reagent to lyse red blood cells, and to form a blood sample mixture,
    (b) measuring said blood sample mixture by a DC impedance measurement to obtain a blood cell distribution,
    (c) differentiating nucleated blood cells using said blood cell distribution obtained in step (b) to obtain an improved separation among cell types using a non-focused flow aperture having an aperture aspect ratio of length versus width of about 1.2 and greater, and
    (d) reporting subpopulations of nucleated blood cells in said blood sample.

2. The method of claim 1 wherein the subpopulations of nucleated blood cells comprise nucleated red blood cells and white blood cells.

3. The method of claim 1 wherein the subpopulations of nucleated blood cells comprise subpopulations of white blood cells.

4. The method of claim 1 wherein said mixing a blood sample with a lytic reagent comprises diluting said blood sample with a blood diluent to form a diluted blood sample, and mixing said diluted blood sample with said lytic reagent.

5. The method of claim 1 wherein said mixing a blood sample with lytic reagent comprises mixing said blood sample with a lytic reagent containing a salt to simultaneously dilute and lyse said blood sample.

6. The method of claim 1 further comprising measuring spectrophotometric absorbance of said blood sample mixture at a predetermined wavelength of a hemoglobin chromogen formed upon lysing said blood sample, and reporting hemoglobin concentration of said blood sample.

\* \* \* \* \*